United States Patent [19]

Sloane

[11] Patent Number: 5,619,991
[45] Date of Patent: Apr. 15, 1997

[54] DELIVERY OF MEDICAL SERVICES USING ELECTRONIC DATA COMMUNICATIONS

[75] Inventor: Neil J. A. Sloane, Highland Park, N.J.

[73] Assignee: Lucent Technologies Inc., Murray Hill, N.J.

[21] Appl. No.: 429,419

[22] Filed: Apr. 26, 1995

[51] Int. Cl.$^6$ .................................................. A61B 5/00
[52] U.S. Cl. ............................................................ 128/630
[58] Field of Search .................................... 128/630, 898, 128/903, 904; 364/413.01–413.12

[56] References Cited

U.S. PATENT DOCUMENTS

| | | | |
|---|---|---|---|
| 4,838,275 | 6/1989 | Lee | 128/904 X |
| 5,216,596 | 6/1993 | Weinstein | 364/413.02 |
| 5,441,047 | 8/1995 | David et al. | 128/904 X |
| 5,462,051 | 10/1995 | Oka et al. | 128/904 X |
| 5,469,353 | 11/1995 | Pinsky et al. | 364/413.01 |

OTHER PUBLICATIONS

Rita Rubin, "Can't reach your doctor: Try E–mail," *U.S. News & World Report*, 82–83 (Feb. 13, 1995).
David Bennahum, "Docs for Docs," *Wired*, 10, 12, 14 (Mar. 1995).

*Primary Examiner*—Angela D. Sykes
*Assistant Examiner*—Samuel Gilbert
*Attorney, Agent, or Firm*—Ronald D. Slusky

[57] ABSTRACT

Patient disease is diagnosed and/or treated using electronic data communications between not only the physician and his/her patient, but via the use of electronic data communications between the physician and one or more entities which can contribute to the patient's diagnosis and/or treatment, such electronic data communications including information that was priorly received electronically from the patient and/or was developed as a consequence of an electronic messaging interaction that occurred between the patient and the physician. Such other entities illustratively include a medical diagnostic center and an epidemiological database computer facility which collects epidemiological transaction records from physicians, hospitals and other institutions which have medical facilities, such as schools and large businesses. The epidemiological transaction record illustratively includes various medical, personal and epidemiological data relevant to the patient and his/her present symptoms, including test results, as well as the diagnosis, if one has already been arrived at by the e-doc. The epidemiological database computer facility can correlate this information with the other epidemiological transaction records that it receives over time in order to help physicians make and/or confirm diagnoses as well as to identify and track epidemiological events and/or trends.

7 Claims, 4 Drawing Sheets

FIG. 3

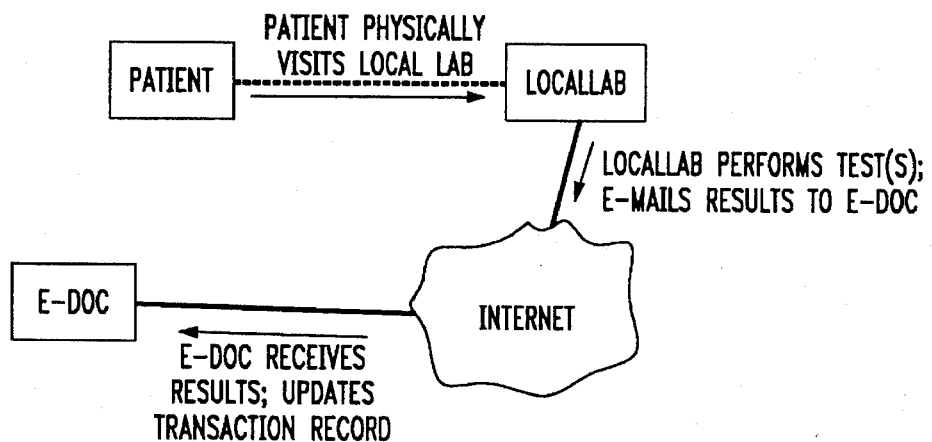

FIG. 4

| E-DOC PATIENT RECORD DATABASE | | | | |
|---|---|---|---|---|
| $ID_1$ | NAME, ETC. | BILLING DATA | DEMOGRAPHIC DATA | FAMILY ID'S |
| $ID_2$ | NAME, ETC. | BILLING DATA | DEMOGRAPHIC DATA | FAMILY ID'S |
| ⋮ | ⋮ | ⋮ | ⋮ | ⋮ |
| $ID_N$ | NAME, ETC. | BILLING DATA | DEMOGRAPHIC DATA | FAMILY ID'S |

FIG. 5

| | E-DOC PATIENT TRANSACTION DATABASE | | |
|---|---|---|---|
| 1 | TRANSACTION # | POINTER TO PATIENT RECORD | TRANSACTION TRAIL |
| 2 | TRANSACTION # | POINTER TO PATIENT RECORD | TRANSACTION TRAIL |
| ⋮ | ⋮ | ⋮ | ⋮ |
| N | TRANSACTION # | POINTER TO PATIENT RECORD | TRANSACTION TRAIL |

| | CDC EPIDEMIOLOGICAL TRANSACTION DATABASE | | |
|---|---|---|---|
| 1 | TRANSACTION # | ABBREVIATED PATIENT RECORD | TRANSACTION TRAIL |
| 2 | TRANSACTION # | ABBREVIATED PATIENT RECORD | TRANSACTION TRAIL |
| ⋮ | ⋮ | ⋮ | ⋮ |
| M | TRANSACTION # | ABBREVIATED PATIENT RECORD | TRANSACTION TRAIL |

DELIVERY OF MEDICAL SERVICES USING ELECTRONIC DATA COMMUNICATIONS

BACKGROUND OF THE INVENTION

The present invention relates to the delivery of medical services.

More and more people have begun to use electronic data communications—such as electronic mail, or e-mail—as a means of communication with others. Indeed, patients and doctors have begun to communicate in this way. See, for example, "Can't reach your doctor? Try E-mail," U.S. News and World Report, Feb. 13, 1995, p. 82. This is advantageous from the patient perspective because it avoids such phenomena and petty annoyances as long waits in the doctor's waiting room, the risk of picking up infections from other patients, etc. Doctors who use e-mail report that it enables them to, for example, have a chance to think through their responses to patient questions. Moreover, both doctors and patients put the elimination of "telephone tag" high on their lists of the advantage of this type of doctor/patient interaction.

Another advantageous aspect of electronic communication in the medical context is the emergence of various on-line services available to physicians and/or consumers which can help diagnose and recommend treatments for diseases—particularly rare diseases with which the typical family practitioner may not be familiar.

Also known in the prior art is the notion of the "virtual patient record," as described, for example, by David Bennahum in "Docs for Docs," *Wired,* March, 1995. Bennahum describes the notion of taking patient records out of paper form and putting them into "mobile bundles of bits that can be easily shipped around the country, from hospital to doctor to pharmacy to insurance company."

SUMMARY OF THE INVENTION

I have recognized that current medical delivery systems have only begun to scratch the surface in terms of ways in which existing electronic data communications technology can be used to more efficiently and effectively bring the body of medical knowledge and skill, as well as relevant epidemiological considerations, to bear on the diagnosis and treatment of disease and illness.

In accordance with the present invention, the process by which patient disease is diagnosed and/or treated using electronic data communications is enhanced via the use of electronic data communications between the physician and one or more entities which can contribute to the patient's diagnosis and/or treatment, such electronic data communications including information that was priorly received electronically from the patient and/or was developed as a consequence of a prior communication between the patient and the physician. The electronic data communications can be, for example, in the form of addressed messages, e.g., e-mail, or could be in the form of a direct data exchange between two endpoints, e.g., a physician inputing data during a query/response session from his/her personal computer keyboard directly into a remote computer system in which the physician has "logged in."

Thus a physician using electronic data communications in his/her practice—referred to herein as an electronic doctor, or "e-doc"—may, in accordance with an aspect of the invention, use electronic dam communications to instruct a medical diagnostic center, laboratory, or testing center to expect the arrival of the patient in question; to perform certain prescribed tests when the patient arrives; and to electronically message the test results (such as a blood test, sputum analysis or throat culture, etc.) or any images that may have been created (such as an X-ray, MRI scan, CT scan, etc.) back to the e-doc, whereupon the e-doc can use electronic data communications to transmit to the patient a course of treatment selected in response to the test results.

The e-doc may, in accordance with another aspect of the invention, use electronic data communications to send a prescription for medicine to the patient's pharmacy or to call for an ambulance.

In accordance with another aspect of the invention, the e-doc may use electronic data communications to submit an "epidemiological transaction record" to an epidemiological database computer facility which collects such records not only from e-docs, but, illustratively, also from hospitals and other institutions which have medical facilities, such as schools, large businesses, shopping malls, religious institutions, military bases, and prisons. The epidemiological transaction record illustratively includes various medical, personal and epidemiological data relevant to the patient and his/her present symptoms, including test results, as well as the diagnosis, if one has already been arrived at by the e-doc. The epidemiological database computer facility can correlate this information with the other epidemiological transaction records that it receives over time in order to help e-docs who have not been able to make a diagnosis to arrive at one—or in order to confirm a diagnosis that an e-doc has made. For example, if a food poisoning epidemic breaks out in a particular locale, the epidemiological database computer facility—as it begins to receive from that locale epidemiological transaction records in which "food poisoning" is listed as being at least the tentative diagnosis—is in a position to return an electronic message to an e-doc submitting such an epidemiological transaction record a suggestion that food poisoning be considered as a likely source of the patient's problems.

BRIEF DESCRIPTION OF THE DRAWING

FIG. 3 shows interactions between two of the entities shown in FIG. 1, specifically the so-called e-doc office and the so-called LocalLab;

FIG. 4 shows patient records in a database maintained within the computer located at the e-doc office;

FIG. 5 shows patient transaction records in a database maintained within the computer located at the e-doc office;

DETAILED DESCRIPTION

Figure 1:
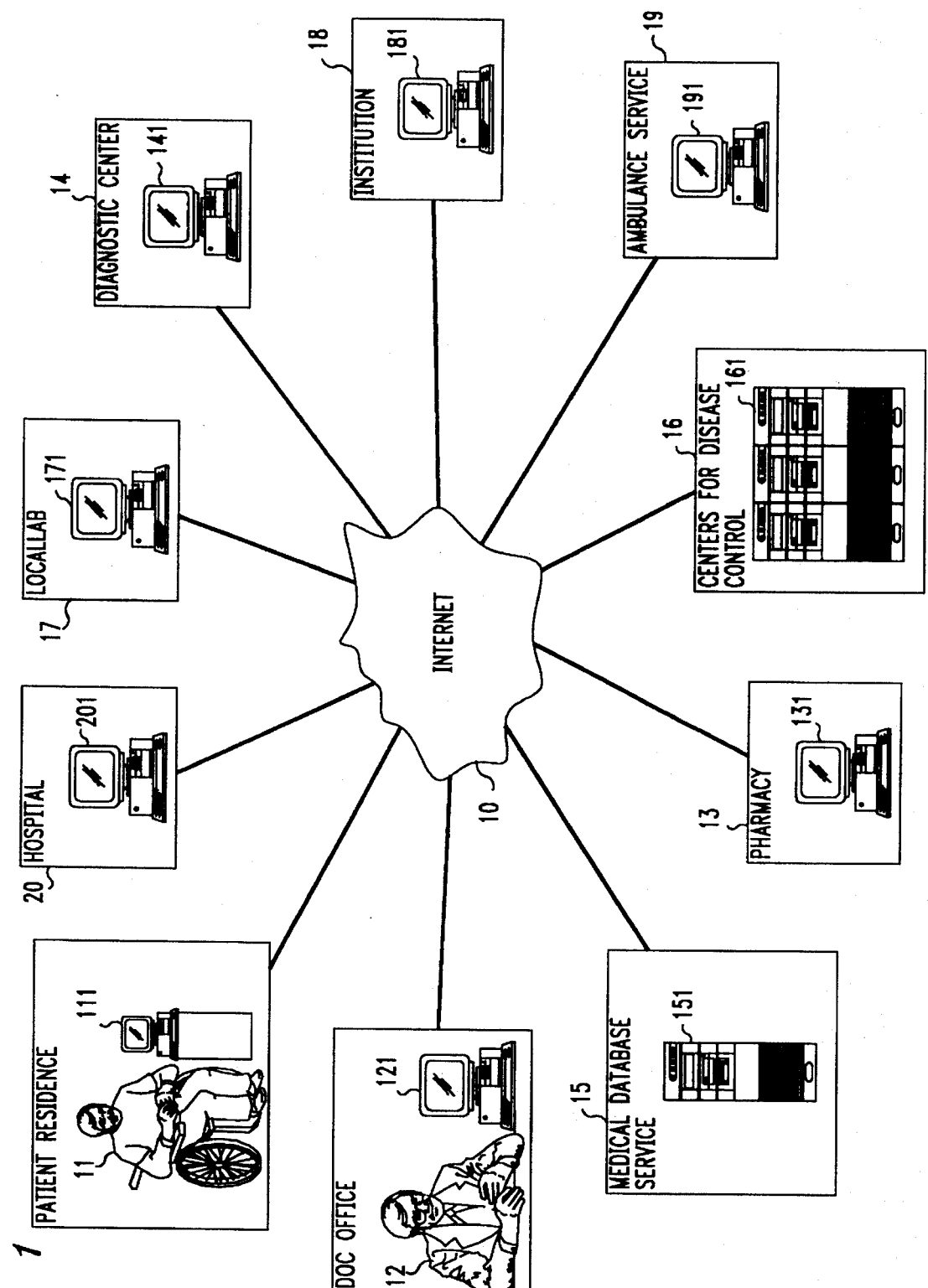
FIG. 1 shows an illustrative system in which the present invention is performed.

FIG. 1 shows a number of entities involved in the delivery of health care, all interconnected via respective links to a communications network, illustratively the so-called Internet. More specifically, the FIG. 1 shows Internet 10 itself to which are connected to a personal computer 111 at the residence of a patient 11; a personal computer 121 at the office of a physician 12 who delivers medical services for at least a segment of his/her patients using the principles of the present invention—referred to herein as an "electronic doctor," or e-doc; a personal computer 131 at a pharmacy 13; a personal computer 141 at diagnostic center 14, which illustratively carries out medical tests of the type which requires expensive equipment, such as CT scanners, MRI machines, etc.; a personal computer 201 at a hospital 20; a personal computer 191 at ambulance service 19; and a time-shared minicomputer 151 at medical data base service 15 which is available to physicians and/or consumers to help diagnose and recommend treatments for diseases—particularly rare diseases with which the typical family practitioner may not be familiar.

Also connected to the Internet are computers at two further entities whose presence in this system play a central role in the carrying out of the invention. One of these is a mainframe computer 161 at the Centers for Disease Control 16 in Atlanta, Ga.—an agency of the United States government. The other is a personal computer 171 at small medical facility 17, which I refer to as a LocalLab. The latter serves as a convenient, easily accessible facility at which routine medical tests can be performed such as blood tests, throat cultures, urinalysis, etc. LocalLab 17 may exist exclusively to perform such tests or, alternatively, could be a walk-in so-called medical emergency office which, in addition to performing such tests, includes on-staff physicians who treat walk-in patients.

Also connected to Internet 10 is a personal computer 181 at institution 18, which is a school, business, shopping mall, religious institution, military base, prison, or other institution which has an on-site nurse, medical department, etc.

It will be realized that, with the exception of CDC 16 and, perhaps medical database service 15, each of the entities depicted in FIG. 1 is representative of many similar such entities (e.g., multiple e-doc locations) dispersed throughout a community or, indeed, the country or the world.

In preferred embodiments, at least some of the aforementioned computers—particularly those located at patient and e-doc locations, are capable of supporting concurrent voice and/or video communications currently with the data communications so that the patient and e-doc can communicate aurally and/or visually in real time as needed. Typically, the data and voice/video communications will be displayed and/or managed in respective "windows" displayed on the various computer screens.

Figure 2:
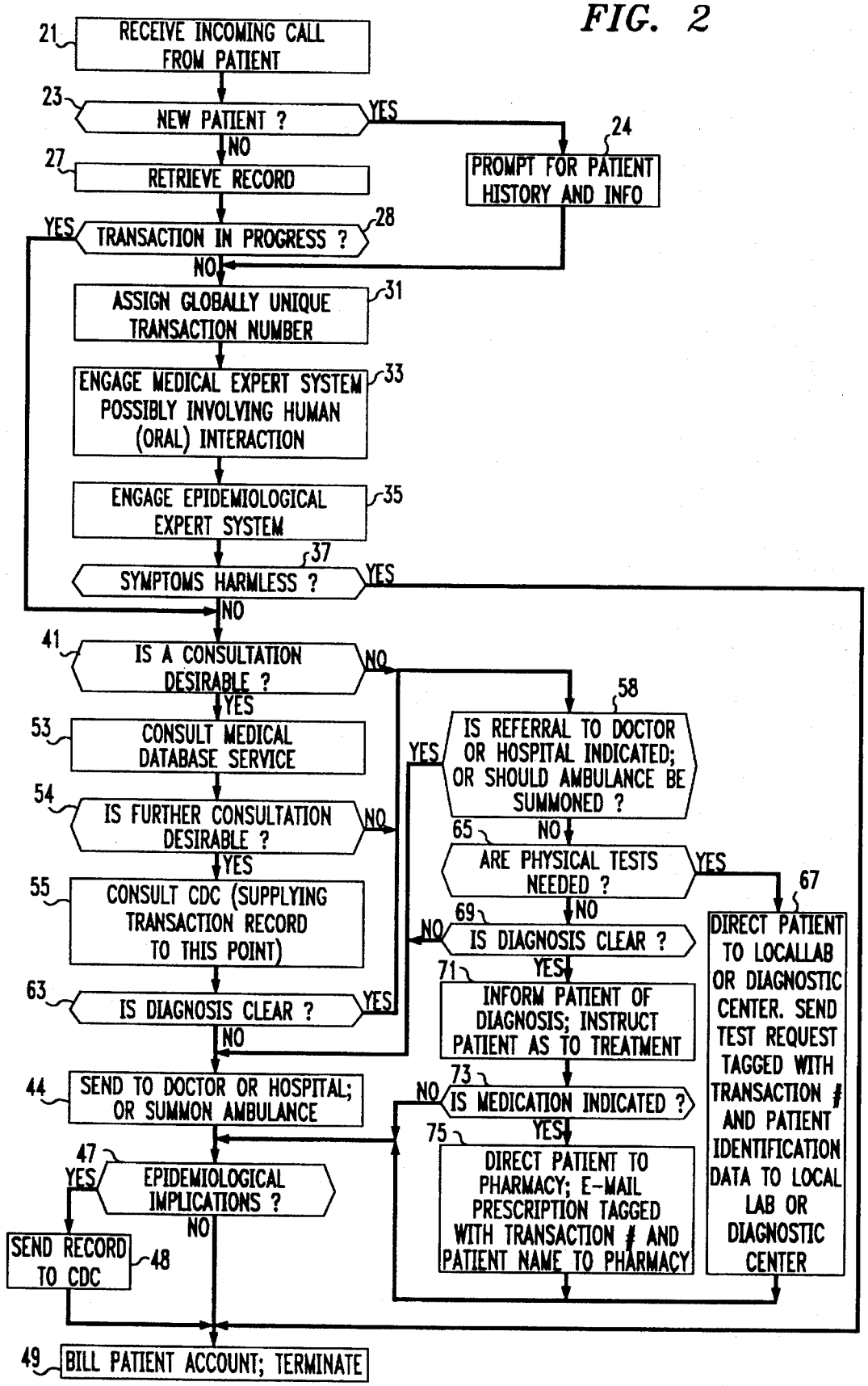
FIG. 2 shows a flowchart of activities undertaken in the system of FIG. 1.

Assume now that patient 11 has a medical problem and wishes to consult with e-doc 12 to obtain advice and/or treatment. To this end, the patient initiates a data call from the patient's personal computer 111 to the e-doc's computer 121. As shown in the flowchart of FIG. 2, the e-doc computer initially receives the incoming call from the patient at block 21. The patient is then prompted for a patient ID number so as to determine whether this patient has a pre-existing relationship with e-doc 12. If, as determined at block 23, this is new patient, the computer prompts the caller for a patient history and other information (block 24), thereby obtaining such data as name, address, billing and insurance information, and previous illnesses and surgeries. Otherwise, the computer proceeds to retrieve the pre-existing patient record at block 27. Ignoring block 28 for the present, an identification number for this call—referred to herein as a "transaction number" is now generated at block 31. For reasons that will become apparent as this description continues, the transaction number is globally unique, meaning that this number uniquely distinguishes this transaction from any other transaction initiated at this or any other e-doc location.

At this point, the e-doc computer 121 begins to execute a software-based medical expert system of known type, as indicated at block 33. This system prompts the caller for symptoms and, following an internal logic tree, asks follow-up questions design to elicit all the information necessary for the medical expert system itself, or for the e-doc to (hopefully) arrive at a diagnosis as to what ails the patient.

As part of this interaction, a human attendant, such as a nurse or perhaps the e-doc himself, may come onto the connection using the voice and/or video capabilities of the patient's and e-doc's computers if the expert system determines that this is appropriate. Indeed, in the patient e-doc communications described below, any interaction between the patient and e-doc's office may include real-time voice and/or video conversations between the patient and the e-doc instead of, or in addition to, a text-based interaction. Such real-time conversations may be initiated by, for example, the e-doc computer, as just suggested, or by the patient, who may provide an indication during a text-based interchange that a human-to-human interaction is desired. Thus, it is to be understood that any indication hereinbelow of information and/or instructions given by e-doc 12 to patient 11 (e.g., "go to LocalLab 17 for a blood test") may be accomplished by a textual message or in a real-time voice and/or video conversation.

Once the interaction with the medical expert system has been completed, a second, epidemiological expert system is invoked, as indicated at block 35. This system is designed to elicit information from the patient which may be significant from an epidemiological standpoint. The use of such information will become clear as this description continues. Thus, for example, the epidemiological expert system may ask the caller where he/she has eaten recently and what was eaten; whether he/she has traveled recently and, if so, to where and when; the name of a cruise ship on which the caller may have traveled during the trip; the name of any professional meeting or conference that may have been attended; etc. The epidemiological expert system may be stored directly on the e-doc's computer. Alternatively, that computer might electronically couple in to its interaction with the patient an epidemiological expert system residing on another computer, such as CDC computer 161. An advantage of that approach is that the CDC computer, being aware of certain epidemiological events that are going on in the country at that time by virtue of its analysis of recently received epidemiological transaction records, as described below, can tailor the questions that it asks based on that knowledge.

Based on the information thus elicited, a number of diagnostic scenarios are possible. As shown at block 37, it may be determined that the symptoms reported are "harmless," that is, not evidencing any disease or disorder that needs treatment. If this is the case, the caller is so informed and, as indicated at block 49, the patient account is billed and the session is terminated.

Assuming that the symptoms are not "harmless," it is then determined either by the medical expert system executing within computer 121, or by e-doc 12, whether a consultation is desirable. A consultation may be desirable either because, based on the information at hand, the diagnosis of the medical problem afflicting the caller is not clear or if, confirmation of a tentative diagnosis is desired. Assume, on the one hand, that further consultation is not required. Assume, moreover, that, as determined at block 58, the problem is one for which it appears that physical examination by a doctor or hospital is required, e.g., it appears that the patient may be experiencing a coronary event. In that event, then the patient will be instructed, as indicated at block 44, to either a) proceed to a doctor's office—e-doc's office or some other, b) go to a hospital, or c) await the arrival of an ambulance from ambulance service 19, which the e-doc will summon e-mail or via a regular voice telephone call.

If, as now determined at block 47, the patient's condition has possible epidemiological implications, e.g., it is an apparent illness as opposed to, for example, a broken bone, a so-called "epidemiological transaction record" described in further detail below is transmitted to CDC computer 161 at block 48, and whether or not that is the case, the e-doc's computer finally proceeds at block 49 to a) bill the patient's account and b) terminate the transaction.

Returning to block 41, assume that e-doc 12 wishes to consult with medical database service 15 before rendering a diagnosis. E-doc 12 will inform patient 11 that he/she needs some time to confirm a diagnosis and will invite the patient to either a) maintain the connection (while e-doc accesses service 15 or even possibly CDC 16 as described below) or b) to terminate the call at this time with an indication that either the patient should call e-doc again later or that e-doc will call the patient back. E-doc 12 will thereupon connect to, and interact with medical database service 15, as indicated at block 53. Based on that interaction, e-doc 12 may determine as indicated in block 54 that further consultation is not needed but that, rather, the process can immediately proceed to either a) patient referral to a doctor or hospital at block 58 or b) physical tests at block 65. If that is the case, the patient is given instructions along these lines—either immediately if the original connection had been maintained, or in the subsequent call made to or by the patient.

Assume, however, that even further consultation is desired—again either because the diagnosis is still not clear or because e-doc 12 simply wishes to have further verification of a tentative diagnosis. In this case, CDC computer 161 may be consulted, as indicated at block 55. The CDC computer may include, for example, a more sophisticated expert system of the type used by database service 15. More importantly, however, the CDC computer may be able to provide a diagnosis based on an epidemiological phenomena that it has been able to discern based on epidemiological transaction records that have been sent to it by e-docs, hospitals, etc., over the recent past. Although this is described in more detail hereinbelow, a key example is the case where the patient's symptoms are consistent with diagnoses that have already been confirmed for patients in patient 11's geographical area, e.g., an outbreak of food poisoning in the local area.

If, as determined at block 63, the diagnosis is still not clear at this point, or if the diagnosis is clear but indicates that this is something that e-doc 12 cannot treat per block 58, the patient is, again, sent to a doctor or hospital at block 44, followed by billing and call termination at block 49. Otherwise, the process proceeds to block 65, at which it is determined whether it is desirable to have certain physical tests performed either at diagnostic center 14 or LocalLab 17. In the predominant number of the cases, the facilities of LocalLab 17 will be adequate, LocalLab 17 being equipped to perform a wide range of conventional medical tests—blood, urine, sputum, etc—as well as to provide inoculations, e.g., tetanus, if these are indicated.

Assuming that the services of diagnostic center 14 or LocalLab 17 are indicated, the patient is directed by e-doc 12, as indicated at block 67, to proceed thereto in order to obtain the necessary tests and/or inoculations. E-doc 12 will, concurrently, notify LocalLab 17 via e-mail to expect the patient. The e-mail message, more particularly, will specify the tests and/or vaccines desired, as well as the transaction number and patient identification data. As shown more particularly in FIG. 3, LocalLab 17, upon obtaining the test results and/or performing the desired inoculations, will transmit an e-mail message back to e-doc 12, giving test results and/or confirming the administration of the inoculations, in a return message which also includes the transaction number. (The test results could be, for example, in text form, e.g., a blood count, or could be a digitized/encoded image e.g., of an X-ray.) E-doc's computer 121, upon receiving the information, inserts it into the transaction record and forwards a copy of an updated epidemiological transaction record, as described below, to CDC 16.

Patient 11 will have been instructed to re-contact e-doc at an appropriate time after the tests have been administered and e-doc's computer 121 will receive the new call at block 21. Since a transaction is in progress, as determined at block 28, the process will pick up at block 65 when the patient calls back. It may be the case that further tests physical tests are needed, and the sequence of steps indicated by blocks 65 and 67 may be repeated one or more times. Ultimately, however, all tests that are needed will have been completed. If the diagnosis is still not clear at this point, as determined at block 69, referral is again made to a doctor or hospital at block 44, followed by billing and terminating the call at block 49.

Otherwise, with the diagnosis now being clear to e-doc 12 based on the described symptoms and/or test results, the process proceeds to block 71 at which point the patient is informed of the diagnosis and is instructed about his/her treatment. Advantageously, since the communications can be in textual form—at least in part—a comprehensive description of exactly what the patient is to do under a variety of situations that may arise during the recovery period can be provided to, and indeed captured by, the patient's computer 111 for later reference. Moreover, because e-doc 12 has access to records of a large number of similar cases—both from his own computer and/or CDC's, quite precise information can be given to the patient about such matters as the expected duration of his/her illness and the likely severity under normal circumstances of the symptoms on each day of the illness.

Finally, if medications are to be prescribed as detailed at block 73, then as indicated at block 75 a prescription can be e-mailed to pharmacy 13 tagged with the transaction number and patient data and the patient directed to pick up his/her medication thereat.

E-doc computer 121 includes at least two databases. As shown in FIG. 4, one of those databases contains individual patient records. Specifically, there is a database record for each patient which includes such fields as a patient identification number (ID), such conventionally requested patient information as the patient name and address and billing (and insurance) information, as well as the patient's preferred pharmacy, nearest LocalLab location, etc. Advantageously, moreover, a patient record illustratively also includes a wide range of demographic information which may be of value to the CDC computer in terms of identifying epidemiological trends among certain segments of the population. Thus the demographic data in the patient record may include not only such information that is typically found in a doctor's patient record as height, weight, sex, etc, but also such further demographic information as occupation; avocations; dietary peculiarities; information about the person's residence, such as the type of heating system used, nearness to high-voltage power lines; whether the person does or used to smoke; whether the person uses a portable cellular phone etc. any of which might have epidemiological ramifications. This information, combined with answers to questions solicited at blocks 33 and 35, as described above, could be meaningful in terms of the CDC computer discerning epidemiological trends. The patient record also illustratively includes the patient identification numbers of members of the patient's family, which may also be relevant in diagnosis since, for example, members of a particular family or household may tend to have similar medical problems and/or susceptibilities.

Another database in the e-doc's computer is shown in FIG. 5. This database contains so-called patient transaction records—one for each new transaction represented by the flowchart of FIG. 2. Each patient transaction record includes the aforementioned transaction number; a pointer to the patient record for the patient in question stored in the patient record database; and a so-called transaction trail. The latter is simply a listing of all the steps performed per the flowchart of FIG. 2, as well as all associated data that may have been gathered including, for example, symptom information, epidemiological information that was solicited, test results, medications prescribed, diagnoses. The various elements of the transaction trail are date- and time-stamped and are added to the patient transaction record as the steps are performed and/or the associated data, e.g., test results, are received by the e-doc computer. Advantageously, the transaction record should also include follow-up and outcome information so that particular sets of symptoms and courses of treatment can be correlated with other transaction records either within the e-doc's computer or CDC computer 161, as described more fully below.

Figures 6, 7:
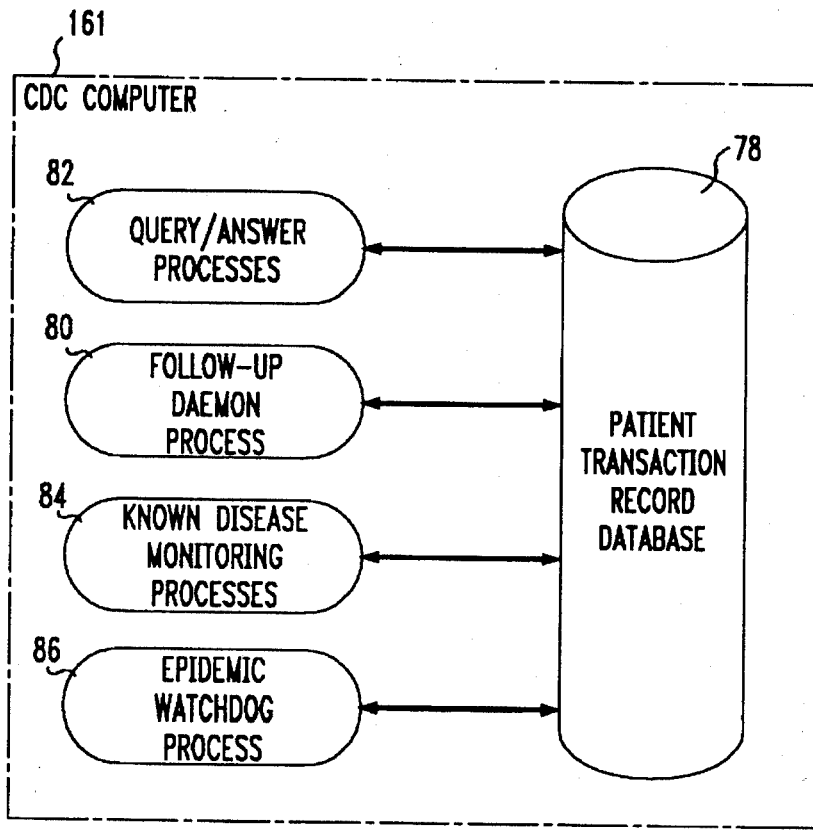
FIG. 6 shows epidemiological transaction records collected in a database maintained within a computer located at another one of the entities, specifically the Centers for Disease Control (CDC)
FIG. 7 is a conceptual view of a computer located at CDC.

FIG. 6 depicts a database within CDC computer 161 containing what I refer to as "epidemiological transaction records," specifically, epidemiological transaction records that have been sent to computer 161 over some predefined period of time, e.g., three months.

An epidemiological transaction record contains information taken both from patient records and transaction records created and stored in, for example, e-doc computers. As shown in FIG. 6, an epidemiological transaction record includes the transaction number; an abbreviated patient record, which comprises patient record information that has been edited to exclude epidemiologically irrelevant information and to protect the anonymity of the patient; and the aforementioned transaction trail. Whenever block 48 is encountered in the course of the execution of the process depicted in FIG. 2, and whenever any new information is entered into a patient transaction record in e-doc computer, a new epidemiological transaction record is automatically sent to CDC computer 161, which thereupon replaces its old copy of the record for a new one.

FIG. 7 is a conceptual view of the CDC computer. The computer includes the aforementioned patient transaction record database 78 and a number of computer processes executing in the computer. One of these processes is a so-called daemon 80 which continuously scans the patient transaction records looking for incompleted patient transactions, e.g., transactions for which the outcome (e.g., "recovered after five days") is not recorded. Upon finding such records, the daemon sends e-mail to the originating e-doc or the patient in an attempt to obtain the missing information.

Also executing within the CDC computer are a plurality of query/answer processes 82, each of which services an ongoing call from (typically) an e-doc seeking information, per block 55. In addition, a plurality of processes 84 each continuously monitors the entire database of patient transaction records looking for the known signatures of particular respective diseases of epidemiological interest, e.g., influenza, tuberculosis, bronchitis, strep throat, Legionnaires disease, AIDS, hepatitis, food poisoning, or particular known virulent viruses, such as ebola and other filoviruses. By being able to identify the geographical and sociological distribution of such diseases, CDC is in a better position to carry out its charter of reporting and/or suggesting treatment modalities for such diseases. Additionally, an epidemic watchdog process 86 looks for patterns in the data in an attempt to identify epidemiological events that are not otherwise monitored by processes 84. One or more of processes 84 could be simply a process which correlates specific diagnoses in patient records, e.g. "food poisoning" with their geographical locations.

The foregoing merely illustrates the principles of the invention and many implementational variations are possible.

For example, a patient transaction record may be initiated not only at an e-doc office, but also at, for example, an institution 18—such as a school or business—at such time as when a student or employee may report in to the school nurse or company medical department with medical symptoms of one kind or another. Although the school nurse or medical department may not provide medical diagnosis or treatment to the person, the sending of an epidemiological transaction record containing, for example, patient information and symptom descriptions from the institution's computer 181 to CDC computer 161 may provide the latter with useful information for identifying epidemiological events, as described below.

Moreover, if desired or necessary, the initial contact between a patient and an e-doc may be required to be an in-person meeting in the e-doc's office rather than via an electronic communication. If desired or necessary, the patient could be asked to sign a waiver at that time indicating that he/she understands the limitations of rendering diagnoses using electronic data communications, such as e-marl, and agrees to not hold e-doc liable for any misdiagnoses that might have been avoided by an office visit.

Additionally, instead of connections being made via the Internet, various entities, e.g., a patient and an e-doc, can connect with each other directly via direct modem dial-in.

Moreover, it may be possible for various simple diagnostic tests or procedures to be performed by the patient him/herself, with real-time read-out being provided to the e-doc. For example, the patient may have a stethoscope unit connected into his/her personal computer and can place the stethoscope at particular locations on his/her body under the direction of the e-doc during a real time voice and/or video communication, with the output of the stethoscope being electronically communicated directly from the patient's computer into the e-doc's computer. Blood pressure or other tests could be similarly performed by the patient. It might even be possible for the patient to use a fiber-optic-based-instrument which would allow the e-doc to observe the patient's throat, ear canal, etc., via a video connection. To the extent that the patient is not able to manipulate these devices by him/herself, this could obviously be done by a family member or even by a "roving" nurse employed by the e-doc to visit the patient.

It will thus be appreciated that although the invention is described herein in the context of particular illustrative embodiments, those skilled in the art will be able to devise many varied arrangements embodying the principles of the invention without departing from their spirit and scope.

I claim:

1. A method for use by a medical office, said method comprising the steps of receiving from a patient a description of medical symptoms experienced by that patient, creating, and storing in a memory of a computer, a patient transaction record, said patient transaction record including symptom information indicative of medical symptoms described by said patient, transmitting to a medical testing facility a first outgoing electronic data communication which specifies at least one selected diagnostic test to be performed on said patient, said one diagnostic test being selected in response to at least a first portion of the medical symptoms stored in said memory, receiving from said medical testing facility a first incoming electronic data communication which includes results of said at least one diagnostic test, adding said test results to said patient transaction record stored in said memory, and communicating to said patient information describing a selected course of medical treatment, said course of medical treatment being selected in response to at least a second portion of the information in said patient transaction record, said second portion including said test results and said symptom information.

2. The invention of claim 1 wherein said description of medical symptoms experienced by said patient is received by said medical office in a second incoming electronic data communication.

3. The invention of claim 1 wherein said information describing a selected course of medical treatment is communicated to said patient in a second outgoing electronic data communication.

4. The invention of claim 1 comprising the further steps, performed prior to said step of transmitting said second outgoing electronic data communication, of retrieving at least a third portion of said symptom information from said patient transaction record stored in said memory, transmitting to an epidemiological database computer facility a third outgoing electronic data communication which includes at least said third portion of said symptom information and which further includes epidemiologically significant information about said patient, said epidemiological database computer facility being of a type which stores epidemiological transaction records received from a multiplicity of medical offices, at least some of those epidemiological transaction records including information describing a) medical symptoms of, b) epidemiological information about, and c) diagnoses of medical conditions of, respective patients, and receiving from said epidemiological database computer facility a third incoming electronic data communication which describes at least one diagnosis, said one diagnosis being the same as the diagnosis contained in a plurality of epidemiological transaction records stored in said epidemiological database computer facility, said epidemiological transaction records each including symptoms and epidemiologically significant information which correspond to those included in said third outgoing electronic data communication transmitted to said epidemiological database computer facility.

5. A method for use by a medical office, said method comprising the steps of receiving from a patient a first incoming electronic data communication which describes medical symptoms experienced by that patient, creating, and storing in a memory of a computer, a patient transaction record, said patient transaction record including symptom information indicative of medical symptoms described in said first incoming electronic data communication, transmitting to a medical testing facility a first outgoing electronic data communication which specifies at least one selected diagnostic test to be performed on said patient, said one diagnostic test being selected in response to at least a first portion of the medical symptoms described in said first incoming electronic data communication, receiving from said medical testing facility a second incoming electronic data communication which includes results of said at least one diagnostic test, adding said test results to said patient transaction record stored in said memory, and transmitting to said patient a second outgoing electronic data communication prescribing a selected course of medical treatment, said course of medical treatment being selected in response to at least a second portion of the information in said patient transaction record, said second portion including said test results and said symptom information.

6. The invention of claim 5 comprising the further steps, performed prior to said step of transmitting said second outgoing electronic data communication, of retrieving at least a third portion of said symptom information from said patient transaction record stored in said memory, transmitting to an epidemiological database computer facility a third outgoing electronic data communication which includes at least said third portion of said symptom information and which further includes epidemiologically significant information about said patient, said epidemiological database computer facility being of a type which stores epidemiological transaction records received from a multiplicity of medical offices, at least some of those epidemiological transaction records including information describing a) medical symptoms of, b) epidemiological information about, and c) diagnoses of medical conditions of, respective patients, and receiving from said epidemiological database computer facility a third incoming electronic data communication which describes at least one diagnosis, said one diagnosis being the same as the diagnosis contained in a plurality of epidemiological transaction records stored in said epidemiological database computer facility, said epidemiological transaction records each including symptoms and epidemiologically significant information which correspond to those included in said third outgoing electronic data communication transmitted to said epidemiological database computer facility.

7. A method for use by a medical office, said method comprising the steps of receiving from a patient a first incoming electronic data communication which describes medical symptoms experienced by that patient, creating, and storing in a memory of a computer, a patient transaction record, said patient transaction record including symptom information indicative of medical symptoms described in said first incoming electronic data communication, retrieving at least a portion of said symptom information from said memory, transmitting to an epidemiological database computer facility a first outgoing electronic data communication which includes at least said retrieved portion of said symptom information and which further includes epidemiologically significant information about said patient, said epidemiological database computer facility being of a type which stores epidemiological transaction records received from a multiplicity of medical offices, at least including information describing a) medical symptoms of, b) epidemiological information about, and c) diagnoses of medical conditions of, respective patients, and receiving from said epidemiological database computer facility a second incoming electronic data communication which describes at least one diagnosis, said one diagnosis being the same as the diagnosis contained in a plurality of epidemiological transaction records stored in said epidemiological database computer facility, said plurality of epidemiological transaction records each including symptoms and epidemiologically significant information which correspond to those included in said first outgoing electronic data communication transmitted to said epidemiological database computer facility, and transmitting to said patient a second outgoing electronic data communication prescribing a selected course of medical treatment, said course of medical treatment being selected as a function of said one diagnosis.

* * * * *